US009537102B2

(12) United States Patent
Park et al.

(10) Patent No.: US 9,537,102 B2
(45) Date of Patent: Jan. 3, 2017

(54) FUSED POLYCYCLIC HETEROAROMATIC COMPOUND, ORGANIC THIN FILM INCLUDING COMPOUND AND ELECTRONIC DEVICE INCLUDING ORGANIC THIN FILM

(71) Applicant: Samsung Electronics Co., Ltd., Suwon-Si, Gyeonggi-Do (KR)

(72) Inventors: Jeong Il Park, Seongnam-si (KR); Bang Lin Lee, Suwon-si (KR); Jong Won Chung, Hwaseong-si (KR); Ji Young Jung, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 778 days.

(21) Appl. No.: 13/910,246

(22) Filed: Jun. 5, 2013

(65) Prior Publication Data

US 2013/0320316 A1   Dec. 5, 2013

(30) Foreign Application Priority Data

Jun. 5, 2012   (KR) .................. 10-2012-0060623

(51) Int. Cl.
*H01L 51/00* (2006.01)
*C09K 11/06* (2006.01)
*C07D 495/04* (2006.01)
*H01L 51/05* (2006.01)

(52) U.S. Cl.
CPC .......... *H01L 51/005* (2013.01); *C07D 495/04* (2013.01); *H01L 51/0074* (2013.01); *H01L 51/0541* (2013.01); *H01L 51/0545* (2013.01); *Y02E 10/549* (2013.01)

(58) Field of Classification Search
None
See application file for complete search history.

(56) References Cited

U.S. PATENT DOCUMENTS

| 5,198,153 A | 3/1993 | Angelopoulos et al. |
|---|---|---|
| 5,892,244 A | 4/1999 | Tanaka et al. |
| 5,946,551 A | 8/1999 | Dimitrakopoulos et al. |
| 5,981,970 A | 11/1999 | Dimitrakopoulos et al. |
| 5,998,804 A | 12/1999 | Suh et al. |
| 6,210,479 B1 | 4/2001 | Bojarczuk et al. |
| 6,215,130 B1 | 4/2001 | Dodabalapur |
| 6,232,157 B1 | 5/2001 | Dodabalapur et al. |
| 6,344,660 B1 | 2/2002 | Dimitrakopoulos et al. |
| 6,344,662 B1 | 2/2002 | Dimitrakopoulos et al. |
| 6,913,710 B2 | 7/2005 | Farrand et al. |
| 2008/0142792 A1 | 6/2008 | Park et al. |
| 2009/0043113 A1 | 2/2009 | Park et al. |
| 2011/0253944 A1 | 10/2011 | Han et al. |

FOREIGN PATENT DOCUMENTS

| CN | 101200471 A | 6/2008 |
|---|---|---|
| CN | 102264098 A | 11/2011 |
| EP | 1932847 A1 | 6/2008 |
| JP | 2008300752 A | 12/2008 |
| KR | 10-2008-0100982 | 11/2008 |

OTHER PUBLICATIONS

Machine translation of JP2008-300752. Date of publication: Dec. 11, 2008.*
European Search Report dated Aug. 5, 2013, issued in European Application No. 13170145.0.
Wex, B. et al. "Synthesis of *anti* and *syn* Isomers of Thieno[f,f]bis[1]benzothiophene. Comparison of the Optical and Electrochemical Properties of the *anti* and *syn* Isomers," Journal of Organic Chemistry, v. 70, 2005: pp. 4502-4505.
Chinese Office Action dated Mar. 2, 2016 issued in corresponding Chinese Application No. 201310218190.X (English translation provided).

* cited by examiner

*Primary Examiner* — Andrew K Bohaty
(74) *Attorney, Agent, or Firm* — Harness, Dickey & Pierce, P.L.C.

(57) ABSTRACT

A low-molecular-weight fused polycyclic heteroaromatic compound may have a compact planar structure in which seven or more rings are fused together, and thereby exhibits high charge mobility, and furthermore, enables the use of a deposition process or a room-temperature solution process when applied to devices, therefore realizing improved processibility. An organic thin film and electronic device may include the fused polycyclic heteroaromatic compound.

18 Claims, 3 Drawing Sheets

US 9,537,102 B2

FUSED POLYCYCLIC HETEROAROMATIC COMPOUND, ORGANIC THIN FILM INCLUDING COMPOUND AND ELECTRONIC DEVICE INCLUDING ORGANIC THIN FILM

CROSS-REFERENCE TO RELATED APPLICATION

This application claims priority under 37 U.S.C. §119 to Korean Patent Application No. 10-2012-0060623 filed in the Korean Intellectual Property Office on Jun. 5, 2012, the entire contents of which are incorporated herein by reference.

BACKGROUND

1. Field

Example embodiments relate to a fused polycyclic heteroaromatic compound, an organic thin film including the same, and an electronic device including the organic thin film.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode generated by an applied gate voltage.

Recently, as a material for a channel of the TFT, organic materials, e.g., pentacene or polythiophene, have been studied. In the case of polymer or oligomer organic materials, e.g., F8T2 (poly(9,9-dioctylfluorene-co-bithiophene)) as a polythiophene-based material, and a solution process, e.g., spin casting, may be desirably applied. However, problems of decreased charge mobility and increased off-state leakage current may occur. Further, low-molecular-weight organic materials, e.g., pentacene, may have a relatively high charge mobility of about 3.2 to about 5.0 cm$^2$/Vs or more, but may require a relatively expensive apparatus for vacuum deposition at the time of forming a thin film. Therefore, the low-molecular-weight organic material may be unsuitable for use in the preparation of a film having a relatively large area, and processibility may be undesirable.

Thus, there have been attempts to devise materials for channel layers having increased charge mobility and improved processibility. The related art discloses dimeric bisbenzodithiophene, in which rings may be fused in groups of three and thus increased charge mobility may be realized.

SUMMARY

Example embodiments provide a low-molecular-weight fused polycyclic heteroaromatic compound that has a compact planar structure in which seven or more aromatic rings are fused together, and thereby exhibits higher charge mobility, and furthermore, enables the use of a deposition process or a room-temperature solution process when applied to devices, therefore realizing improved processibility.

Example embodiments also provide an organic thin film including the fused polycyclic heteroaromatic compound. Example embodiments also provide an electronic device including the organic thin film as a carrier transport layer.

According to example embodiments, a fused polycyclic heteroaromatic compound may be represented by the following Chemical Formula 1.

[Chemical Formula 1]

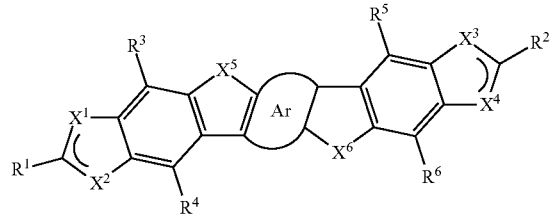

In the above Chemical Formula 1,

Ar is a substituted or unsubstituted C$_6$ to C$_{30}$ aromatic cyclic group, each of X$^1$ to X$^4$ are independently one of O, S, Se, Te, N—R$^a$, and CR$^b$, wherein each of R$^a$ and R$^b$ are independently one of hydrogen, a substituted or unsubstituted linear or branched C$_1$ to C$_{30}$ alkyl group, a substituted or unsubstituted C$_7$ to C$_{30}$ arylalkyl group, a substituted or unsubstituted C$_6$ to C$_{30}$ aryl group, a substituted or unsubstituted C$_1$ to C$_{30}$ alkoxy group, a substituted or unsubstituted C$_6$ to C$_{30}$ aryloxy group (—OR$^{11}$, wherein R$^{11}$ is a substituted or unsubstituted C$_6$ to C$_{30}$ aryl group), a substituted or unsubstituted C$_4$ to C$_{30}$ cycloalkyl group, a substituted or unsubstituted C$_4$ to C$_{30}$ cycloalkyloxy group (–OR$^{12}$, wherein R$^{12}$ is a substituted or unsubstituted C$_4$ to C$_{30}$ cycloalkyl group), a substituted or unsubstituted C$_2$ to C$_{30}$ heteroaryl group, an acyl group (—C(═O)R$^{13}$, wherein R$^{13}$ is a substituted or unsubstituted C$_1$ to C$_{30}$ alkyl group), a sulfonyl group (—S(═O)$_2$R$^{14}$, wherein R$^{14}$ is a substituted or unsubstituted C$_1$ to C$_{30}$ alkyl group) and a carbamate group (—NHC(═O)OR$^{15}$, wherein R$^{15}$ is a substituted or unsubstituted C$_1$ to C$_{30}$ alkyl group), at least one of X$^1$ and X$^2$ is selected from O, S, Se, Te, and N—R$^a$, at least one of X$^3$ and X$^4$ is selected from O, S, Se, Te, and N—R$^a$, each of X$^5$ and X$^6$ are independently one of O, S, Se, Te, N—R$^a$, and CR$^b$R$^c$ wherein each of R$^a$ to R$^c$ are independently one of hydrogen, a substituted or unsubstituted linear or branched C$_1$ to C$_{30}$ alkyl group, a substituted or unsubstituted C$_7$ to C$_{30}$ arylalkyl group, a substituted or unsubstituted C$_6$ to C$_{30}$ aryl group, a substituted or unsubstituted C$_1$ to C$_{30}$ alkoxy group, a substituted or unsubstituted C$_6$ to C$_{30}$ aryloxy group (—OR$^{11}$, wherein R$^{11}$ is a substituted or unsubstituted C$_6$ to C$_{30}$ aryl group), a substituted or unsubstituted C$_4$ to C$_{30}$ cycloalkyl group, a substituted or unsubstituted C$_4$ to C$_{30}$ cycloalkyloxy group (–OR$^{12}$, wherein R$^{12}$ is a substituted or unsubstituted C$_4$ to C$_{30}$ cycloalkyl group), a substituted or unsubstituted C$_2$ to C$_{30}$ heteroaryl group, an acyl group (—C(═O)R$^{13}$, wherein R$^{13}$ is a substituted or unsubstituted C$_1$ to C$_{30}$ alkyl group), a sulfonyl group (—S(═O)$_2$R$^{14}$, wherein R$^{14}$ is a substituted or unsubstituted C$_1$ to C$_{30}$ alkyl group) and a carbamate group (—NHC(═O)OR$^{15}$, wherein R$^{15}$ is a substituted or unsubstituted C$_1$ to C$_{30}$ alkyl group), and each of R$^1$ to R$^6$ are independently one of hydrogen, a halogen (—F, —Cl, —Br or —I), a substituted or unsubstituted linear or branched C$_1$ to C$_{30}$ alkyl group, a substituted or unsubstituted linear or branched C$_2$ to C$_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

The fused polycyclic heteroaromatic compound may be one of fused polycyclic heteroaromatic compounds represented by the following Chemical Formulae 1A to 1G.

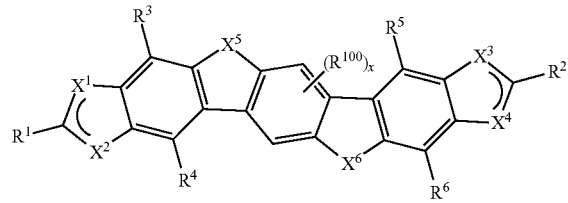

[Chemical Formula 1A]

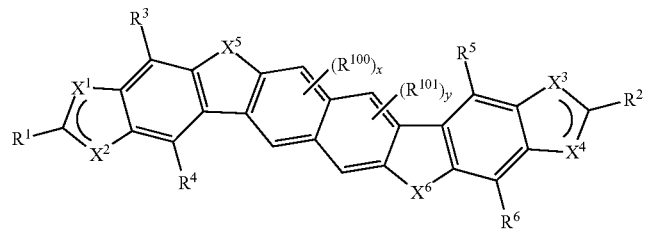

[Chemical Formula 1B]

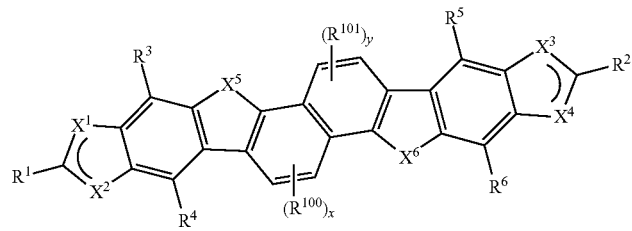

[Chemical Formula 1C]

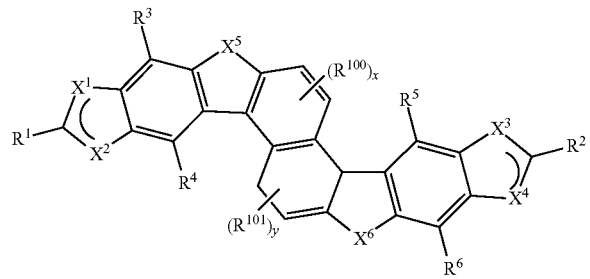

[Chemical Formula 1D]

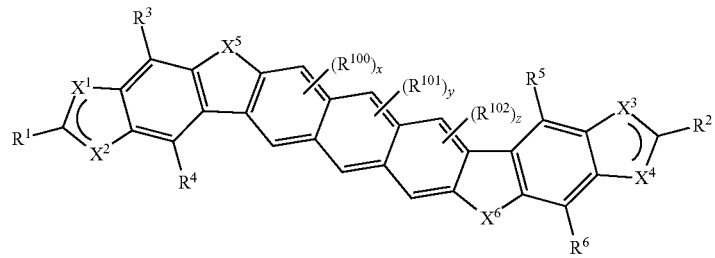

[Chemical Formula 1E]

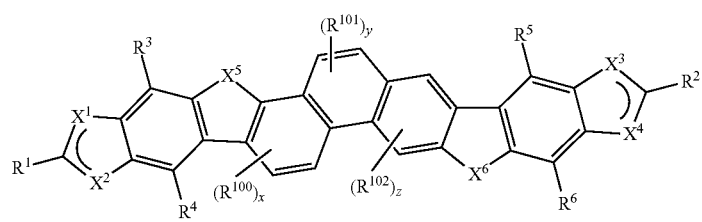

[Chemical Formula 1F]

[Chemical Formula 1G]

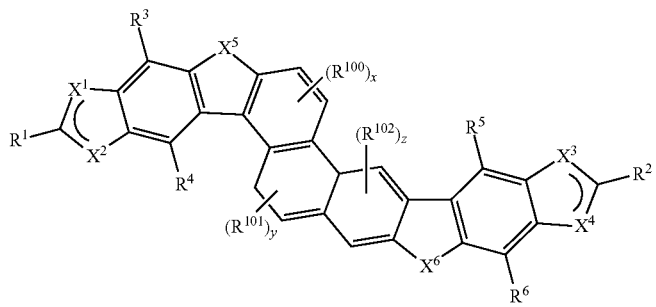

In the above Chemical Formulae 1A to 1G, $X^1$, $X^2$, $X^3$, $X^4$, $X^5$, $X^6$, $R^1$, $R^2$, $R^3$, $R^4$, $R^5$ and $R^6$ are the same as in Chemical Formula 1, each of $R^{100}$ to $R^{102}$ are independently one of hydrogen, halogen (—F, —Cl, —Br or —I), a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, and x, y, and z are integers of 1 or 2.

In Chemical Formula 1, one of $X^1$ and $X^2$ and one of $X^3$ and $X^4$ may be sulfur (S).

The fused polycyclic heteroaromatic compound may have an average molecular weight of about 350 to about 3000.

In Chemical Formula 1, an atom of each of $X^1$ and $X^4$, and $X^2$ and $X^3$ is positioned symmetrically to each other.

In Chemical Formula 1, Ar is one of a substituted or unsubstituted benzene, a substituted or unsubstituted naphthalene, and a substituted or unsubstituted anthracene.

In Chemical Formula 1, each of $R^1$ to $R^6$ are independently one of a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

According to example embodiments, an organic thin film and an electronic device may include the fused polycyclic heteroaromatic compound.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
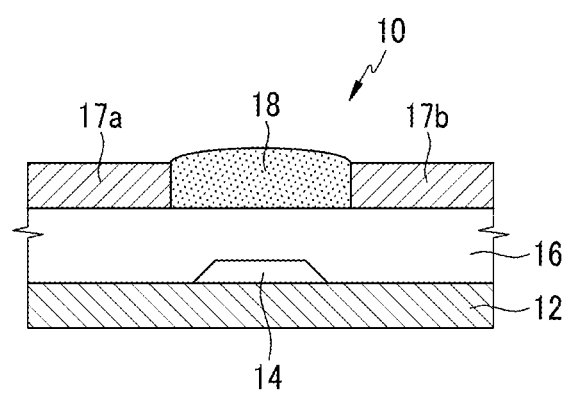
FIG. 1 is a schematic cross-sectional view of a transistor according to example embodiments.

Example embodiments will now be described more fully with reference to the accompanying drawings. However, it should be understood that the examples may be embodied in many different forms and should not be construed as being limited to the embodiments set forth herein. Rather, these embodiments are merely provided so that this disclosure will be more thorough and complete and will assist in fully conveying the concept of example embodiments to those of ordinary skill in the art. Like reference numerals in the drawings denote like elements, and thus their description in a similar drawing may be omitted for purposes of brevity.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments are described herein with reference to cross-sectional illustrations that are schematic illustrations of idealized embodiments (and perhaps intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

In the drawings, the thickness of layers, films, panels, regions, etc., are exaggerated for clarity.

It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, the term "combination thereof" refers to a mixture, a stacked structure, a composite, or an alloy.

As used herein, when a definition is not otherwise provided, the term "hetero" may refer to one including 1 to 4 heteroatoms selected from N, O, S, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. The term "heterocycloalkyl group" may be at least one non-aromatic ring including a heteroatom, and the term "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, and/or a hexyl group).

The term "alkenyl group" may refer to a linear or branched unsaturated monovalent hydrocarbon group including at least one carbon-carbon double bond (e.g., an ethenyl group).

The term "alkynyl group" may refer to a linear or branched unsaturated monovalent hydrocarbon group including at least one carbon-carbon triple bond (e.g., ethynyl group).

The term "alkoxy group" may refer to an alkyl group that is linked via an oxygen, e.g., a methoxy, an ethoxy, and a sec-butyloxy group.

The term "aryl group" may refer to a monovalent functional group formed by the removal of one hydrogen atom from one or more rings of an arene, e.g., phenyl or naphthyl. The arene may refer to a hydrocarbon having an aromatic ring, and includes monocyclic and polycyclic hydrocarbons wherein the additional ring(s) of the polycyclic hydrocarbon may be aromatic or nonaromatic.

The term "aryloxy group" may refer to an aryl group that is linked via an oxygen, and the aryl group is the same as described above.

The "arylalkyl group" may refer to an aryl group where one hydrogen is substituted with a lower alkylene, e.g., methylene, ethylene, and/or propylene. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "cycloalkenyl group" may refer to a monovalent functional group including at least one ring having a carbon-carbon double bond, wherein all ring members are carbon, e.g., a cyclopentenyl group or a cyclohexenyl group.

The term "cycloalkynyl group" may refer to a stabilized aliphatic monocyclic or polycyclic functional group including at least one carbon-carbon triple bond.

The term "heteroarylalkyl group" may refer to the alkyl group defined above where at least one hydrogen is substituted with a heteroaryl group.

The term "alkylheteroaryl group" may refer to the heteroaryl group defined above where at least one hydrogen is substituted with an alkyl group.

As used herein, when a definition is not otherwise provided, the term "aromatic ring" refers to a functional group in which all atoms in the cyclic functional group have a p-orbital, wherein these p-orbitals are conjugated. For example, the aromatic ring may be a $C_6$ to $C_{20}$ aryl group.

As used herein, when a definition is not otherwise provided, the term "heteroaromatic ring" refers to a functional group including a heteroatom selected from N, O, and S in a ring in which all atoms in the cyclic functional group have a p-orbital, wherein the p-orbital is conjugated. For example, the heteroaromatic ring may be a $C_2$ to $C_{20}$ heteroaryl group.

As used herein, when a definition is not otherwise provided, the term "alicyclic ring" may refer to non-conjugated ring, for example, a $C_3$ to $C_{20}$ cycloalkyl group, a $C_3$ to $C_{20}$ heterocycloalkyl group, a $C_3$ to $C_{20}$ cycloalkenyl group, and/or a $C_3$ to $C_{20}$ heterocycloalkenyl group.

As used herein, when a definition is not otherwise provided, the term "substituted" means that a compound or group is substituted with at least one substituent selected independently from a halogen (—F, —Cl, —Br, or —I), a $C_1$ to $C_{30}$ linear or branched alkyl group, for example, a $C_1$ to $C_{10}$ linear or branched alkyl group, $C_2$ to $C_{30}$ linear or branched alkenyl group, for example, a $C_2$ to $C_{10}$ linear or branched alkenyl group, a $C_2$ to $C_{30}$ linear or branched alkynyl group, for example, a $C_2$ to $C_{10}$ linear or branched alkynyl group, a $C_6$ to $C_{30}$ aryl group, for example, a $C_6$ to $C_{12}$ aryl group, a $C_2$ to $C_{30}$ heteroaryl group, for example, a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+1}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein R and R' are independently one of hydrogen and a $C_1$ to $C_{10}$ alkyl group), an amidino group (—C(=NH)NH$_2$), a nitro group (—NO$_2$), an amide group (—C(=O)N(H)R, wherein R is hydrogen or a $C_1$ to $C_{10}$ alkyl group), an aldehyde group (—C(=O)H), a hydroxyl group (—OH), a sulfonyl group (—S(=O)$_2$R, wherein R is one of hydrogen and a $C_1$ to $C_{10}$ alkyl group), and a carbamate group (—NH$_2$C(=O)OR, wherein R is a $C_1$ to $C_{10}$ alkyl group) instead of hydrogen, provided that the substituted atom's normal valence is not exceeded.

According to example embodiments, a fused polycyclic heteroaromatic compound may have a compact planar structure in which seven or more rings may be fused together in the following Chemical Formula 1.

[Chemical Formula 1]

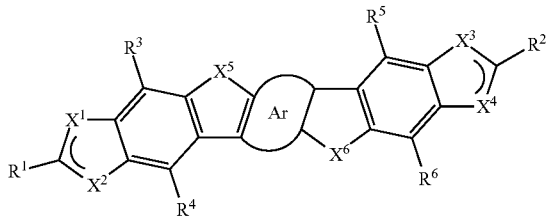

In the above Chemical Formula 1,

Ar is a substituted or unsubstituted $C_6$ to $C_{30}$ aromatic cyclic group, each of $X^1$ to $X^4$ are independently one of O, S, Se, Te, N—$R^a$, and $CR^b$, wherein each of $R^a$ and $R^b$ are independently one of hydrogen, a substituted or unsubstituted linear or branched $C_1$ to $C_{30}$ alkyl group, for example, a substituted or unsubstituted linear or branched $C_1$ to $C_{20}$ alkyl group, a substituted or unsubstituted $C_7$ to $C_{30}$ arylalkyl group, for example, a substituted or unsubstituted $C_7$ to $C_{20}$ arylalkyl group, a substituted or unsubstituted $C_6$ to $C_{30}$ aryl group, for example, a substituted or unsubstituted $C_6$ to $C_{20}$ aryl group, a substituted or unsubstituted $C_1$ to $C_{30}$ alkoxy group, for example, a substituted or unsubstituted $C_1$ to $C_{20}$ alkoxy group, a substituted or unsubstituted $C_6$ to $C_{30}$ aryloxy group, for example, a substituted or unsubstituted $C_6$ to $C_{20}$ aryloxy group (—OR$^{11}$, wherein R$^{11}$ is a substituted or unsubstituted $C_6$ to $C_{30}$ aryl group, for example, a substituted or unsubstituted $C_6$ to $C_{20}$ aryl group), a substituted or unsubstituted $C_4$ to $C_{30}$ cycloalkyl group, for example, a substituted or unsubstituted $C_4$ to $C_{20}$ cycloalkyl group, a substituted or unsubstituted $C_4$ to $C_{30}$ cycloalkyloxy group, for example, a substituted or unsubstituted $C_4$ to $C_{20}$ cycloalkyloxy group (-OR$^{12}$, wherein R$^{12}$ is a substituted or unsubstituted $C_4$ to $C_{30}$ cycloalkyl group, for example, a substituted or unsubstituted $C_4$ to $C_{20}$ cycloalkyl group), a substituted or unsubstituted $C_2$ to $C_{30}$ heteroaryl group, for example, a substituted or unsubstituted $C_2$ to $C_{20}$ heteroaryl group, an acyl group (—C(=O)R$^{13}$, wherein R$^{13}$ is a substituted or unsubstituted $C_1$ to $C_{30}$ alkyl group, for example, a $C_1$ to $C_{20}$ alkyl group), a sulfonyl group (—S(=O)$_2$R$^{14}$, wherein R$^{14}$ is a substituted or unsubstituted $C_1$ to $C_{30}$ alkyl group, for example, a $C_1$ to $C_{20}$ alkyl group), and a carbamate group (—NHC(=O)OR$^{15}$, wherein R$^{15}$ is a substituted or unsubstituted $C_1$ to $C_{30}$ alkyl group, for example, a substituted or unsubstituted $C_1$ to $C_{20}$ alkyl group), at least one of $X^1$ and $X^2$ is selected from O, S, Se, Te, and N—$R^a$, at least one of $X^3$ and $X^4$ is selected from O, S, Se, Te, and N—$R^a$, each of $X^5$ and $X^6$ are independently one of O, S, Se, Te, N—$R^a$, and $CR^bR^c$ wherein each of $R^a$ to $R^c$ are independently one of hydrogen, a substituted or unsubstituted linear or branched $C_1$ to $C_{30}$ alkyl group, for example, a substituted or unsubstituted linear or branched $C_1$ to $C_{20}$ alkyl group, a substituted or unsubstituted $C_7$ to $C_{30}$ arylalkyl group, for example, a substituted or unsubstituted $C_7$ to $C_{20}$ arylalkyl group, a substituted or unsubstituted $C_6$ to $C_{30}$ aryl group, for example, a substituted or unsubstituted $C_6$ to $C_{20}$ aryl group, a substituted or unsubstituted $C_1$ to $C_{30}$ alkoxy group, for example, a substituted or unsubstituted $C_1$ to $C_{20}$ alkoxy group, a substituted or unsubstituted $C_6$ to $C_{30}$ aryloxy group, for example, a substituted or unsubstituted $C_6$ to $C_{20}$ aryloxy group (—OR$^{11}$, wherein R$^{11}$ is a substituted or unsubstituted $C_6$ to $C_{30}$ aryl group, for example, a $C_6$ to $C_{20}$ aryl group), a substituted or unsubstituted $C_4$ to $C_{30}$ cycloalkyl group, for example, a substituted or unsubstituted $C_4$ to $C_{20}$ cycloalkyl group, a substituted or unsubstituted $C_4$ to $C_{30}$ cycloalkyloxy group, for example, a substituted or unsubstituted $C_4$ to $C_{20}$ cycloalkyloxy group (-OR$^{12}$, wherein R$^{12}$ is a substituted or unsubstituted $C_4$ to $C_{30}$ cycloalkyl group, for example, a substituted or unsubstituted $C_4$ to $C_{20}$ cycloalkyl group), a substituted or unsubstituted $C_2$ to $C_{30}$ heteroaryl group, for example, a substituted or unsubstituted $C_2$ to $C_{20}$ heteroaryl group, an acyl group (—C(=O)R$^{13}$, wherein R$^{13}$ is a substituted or unsubstituted $C_1$ to $C_{30}$ alkyl group, for example, a substituted or unsubstituted $C_1$ to $C_{20}$ alkyl group), a sulfonyl group (—S(=O)$_2$R$^{14}$, wherein R$^{14}$ is a substituted or unsubstituted $C_1$ to $C_{30}$ alkyl group, for example, a substituted or unsubstituted $C_1$ to $C_{20}$ alkyl group), and a carbamate group (—NHC(=O)OR$^{15}$, wherein R$^{15}$ is a substituted or unsubstituted $C_1$ to $C_{30}$ alkyl group, for example, a substituted or unsubstituted $C_1$ to $C_{20}$ alkyl group), and each of $R^1$ to $R^6$ are independently one of hydrogen, halogen, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, for example, a substituted or unsubstituted linear or branched $C_2$ to $C_{20}$ alkynyl group, a substituted or unsubstituted $C_7$ to $C_{30}$ arylalkyl group, for example, a substituted or unsubstituted $C_7$ to $C_{20}$ arylalkyl group, a substituted or unsubstituted $C_2$ to $C_{30}$ heteroarylalkyl group, for example, a substituted or unsubstituted $C_2$ to $C_{20}$ heteroarylalkyl group, a substituted or unsubstituted $C_2$ to $C_{30}$ alkylheteroaryl group, for example, a substituted or unsubstituted $C_2$ to $C_{20}$ alkylheteroaryl group, a substituted or unsubstituted $C_5$ to $C_{30}$ cycloalkyl group, for example, a substituted or unsubstituted $C_5$ to $C_{20}$ cycloalkyl group, a substituted or unsubstituted $C_2$ to $C_{30}$ heterocycloalkyl group, for example, a substituted or unsubstituted $C_2$ to $C_{20}$ heterocycloalkyl group, a substituted or unsubstituted $C_6$ to $C_{30}$ aryl group, for example, a substituted or unsubstituted $C_6$ to $C_{20}$ aryl group, and a substituted or unsubstituted $C_2$ to $C_{30}$ heteroaryl group, for example, a substituted or unsubstituted $C_2$ to $C_{20}$ heteroaryl group.

The fused polycyclic heteroaromatic compounds represented by the above Chemical Formula 1 have a structure in which seven or more aromatic rings and heteroaromatic rings are fused. By having a compact planar molecular structure, the fused polycyclic heteroaromatic compound has a uniform and stable oxidation potential when applied to an actual device and shows higher charge mobility because the intermolecular packing and stacking are improved. Thereby, the fused polycyclic heteroaromatic compounds may be more easily synthesized to be effectively applied to a semiconductor material and/or an electron transporting material. In other words, benzene rings are positioned at both sides in the center of two rings containing $X^5$ and $X^6$ linked by an aromatic ring (Ar), and an $X^1$ and $X^2$-containing hetero-ring and an $X^3$ and $X^4$-containing hetero-ring are condensed with the benzene rings in Chemical Formula 1, and thereby the conjugation structure is enlarged and the intermolecular interaction is enhanced.

In addition, by positioning a hetero-ring between benzene rings, the solubility of the fused polycyclic heteroaromatic compound for the organic solvent may be improved. By introducing a $C_{10}$ to $C_{30}$ long aliphatic chain group (e.g., a substituted or unsubstituted $C_{10}$ to $C_{30}$ alkyl group or a substituted or unsubstituted $C_{10}$ to $C_{30}$ alkenyl group) into $R^1$ to $R^6$, solubility of the fused polycyclic heteroaromatic compound for the organic solvent may be improved. Due to the solubility improvement, the fused polycyclic heteroaromatic compound may be simply coated by a solution process at room temperature as well as in a deposition process, and the thin film may be formed in a relatively wide area so the processibility and the workability are improved.

In the above Chemical Formula 1, the same atom at each of $X^1$ and $X^4$, and $X^2$ and $X^3$ may be positioned symmetrically to each other and therefore the packing or stacking characteristics may be enhanced.

In the above Chemical Formula 1, one of $X^1$ and $X^2$ and one of $X^3$ and $X^4$ may be a sulfur atom (S).

In the above Chemical Formula 1 Ar may be a substituted or unsubstituted benzene, a substituted or unsubstituted naphthalene, or a substituted or unsubstituted anthracene.

The fused polycyclic heteroaromatic compound may be one of the fused polycyclic heteroaromatic compounds represented by the following Chemical Formulae 1A to 1G.

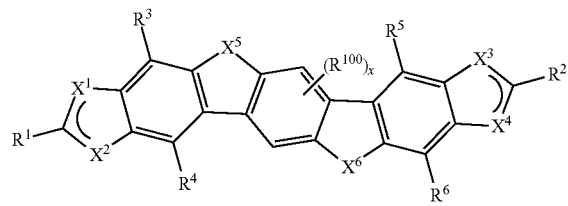

[Chemical Formula 1A]

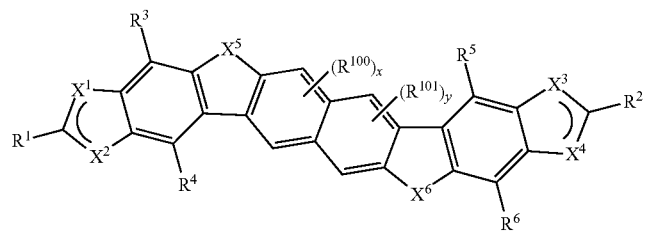

[Chemical Formula 1B]

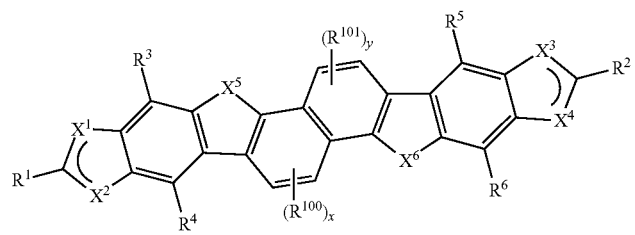

[Chemical Formula 1C]

-continued

[Chemical Formula 1D]

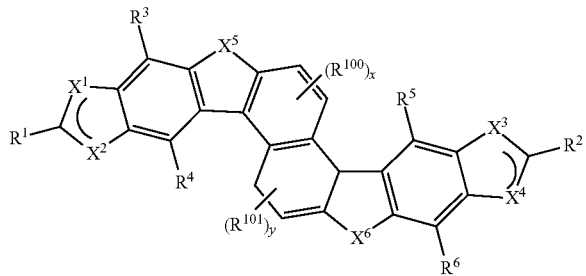

[Chemical Formula 1E]

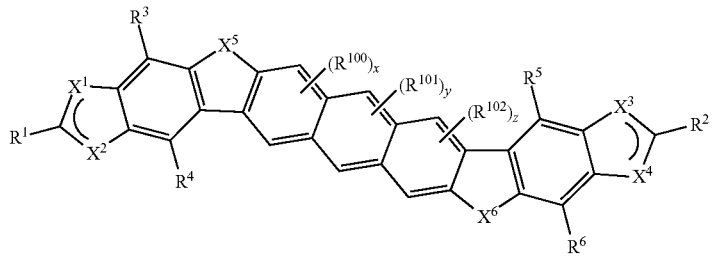

[Chemical Formula 1F]

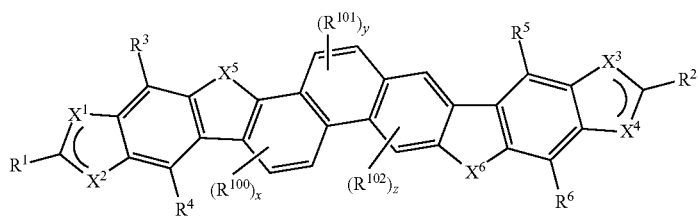

[Chemical Formula 1G]

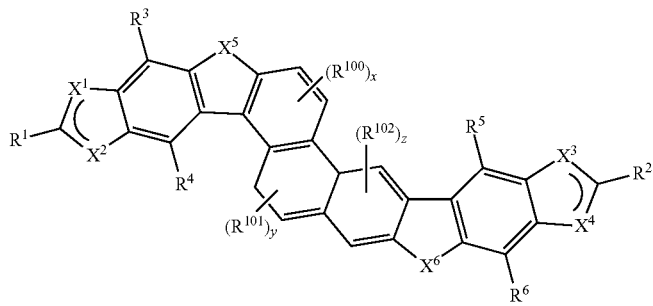

In the above Chemical Formulae 1A to 1G, $X^1$, $X^2$, $X^3$, $X^4$, $X^5$, $X^6$, $R^1$, $R^2$, $R^3$, $R^4$, $R^5$, and $R^6$ are the same as in Chemical Formula 1, each of $R^{100}$ to $R^{102}$ are independently one of hydrogen, halogen (—F, —Cl, —Br or —I), a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, and x, y, and z are integers of 1 or 2.

In the above Chemical Formulae 1A to 1G, one of $X^1$ and $X^2$ and one of $X^3$ and $X^4$ may be a sulfur atom (S).

Examples of the fused polycyclic heteroaromatic compound may include the following compounds (1) to (12).

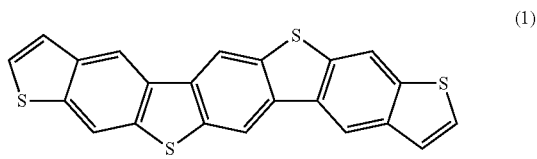

(1)

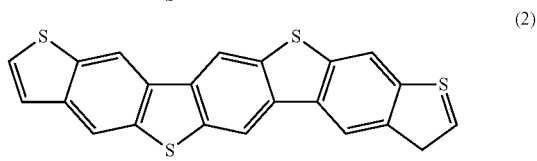

(2)

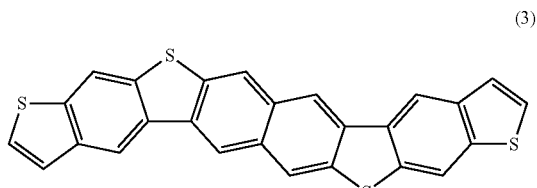

(3)

(4)
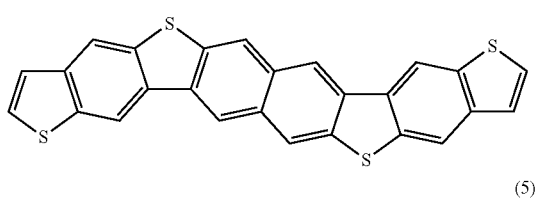

(5)
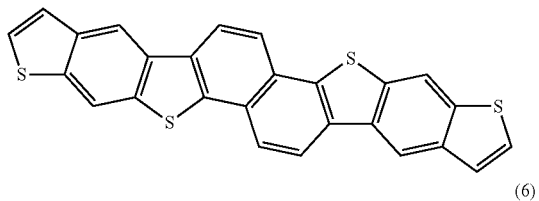

(6)
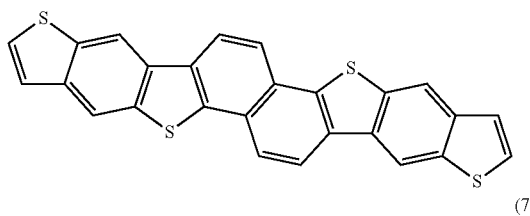

(7)
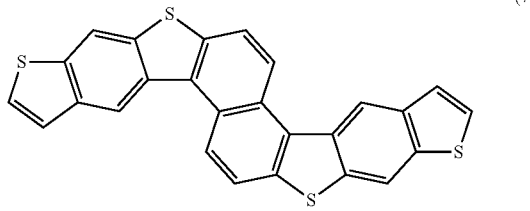

(8)
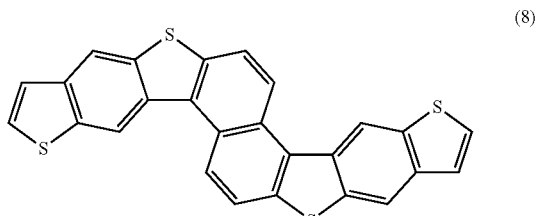

(9)
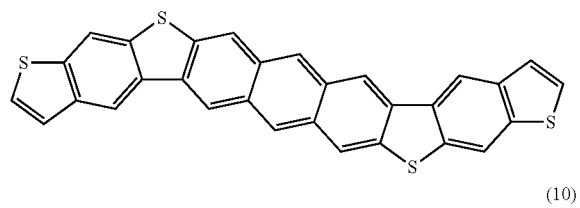

(10)
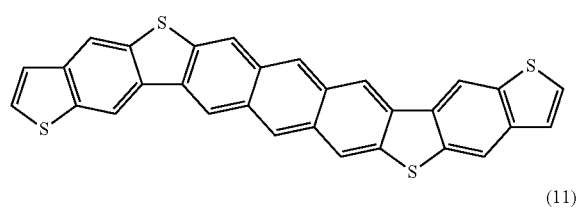

(11)
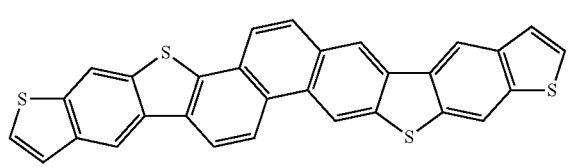

(12)
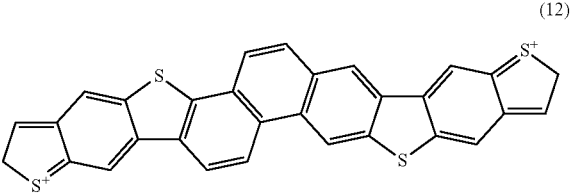

The reorganization energy of compounds (1), (2), (5), and (6) among the compounds (1) to (12) is calculated by using the Gaussian 03 program in DFT B3PW91 6-311G+ (d,p) level, and the results are shown in the following Table 1. For comparison, the reorganization energy of the following compounds ref-1 and ref-2 is also shown in Table 1.

TABLE 1 ref-1
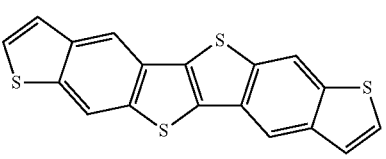 [SMILES: c1cc2cc3c(cc2s1)sc1c2cc4ccsc4cc2sc31]

ref-2
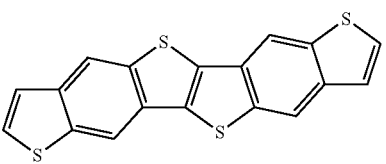 [SMILES: c1cc2cc3sc4c5cc6sccc6cc5sc4c3cc2s1]

| Compound | $E_{HOMO}$ (eV) | $E_{LUMO}$ (eV) | ΔE (eV) | Reorganization Energy (eV) |
|---|---|---|---|---|
| Compound ref-1 | −5.61 | −1.76 | 3.84 | 0.135 |
| Compound ref-2 | −5.57 | −1.99 | 3.57 | 0.162 |
| Compound 1 | −5.69 | −1.93 | 3.75 | 0.095 |
| Compound 2 | −5.69 | −2.10 | 3.59 | 0.096 |
| Compound 5 | −5.68 | −1.89 | 3.79 | 0.086 |
| Compound 6 | −5.66 | −2.04 | 3.62 | 0.105 |

As shown in Table 1, compounds (1), (2), (5), and (6) have lower reorganization energies than compounds ref-1 and ref-2. From the results, the compounds (1), (2), (5), and (6) are expected to have improved charge mobility compared with the compounds ref-1 and ref-2.

The fused polycyclic heteroaromatic compound according to example embodiments may be prepared according to a general method, for example, chemical or electrochemical oxidation synthesis, which is a representative method of polymerizing an aromatic compound or a heteroaromatic compound, or condensation polymerization using a compound of an organic transition element (e.g., nickel or palladium).

For example, the compound of the above Chemical Formula 1 may be obtained by a cyclization reaction of an intermediate compound of the following Chemical Formula 1-1. The cyclization reaction may be performed by the method described in, for example, J. Org. Chem. 2005, 70, 4502-4505.

[Chemical Formula 1-1]

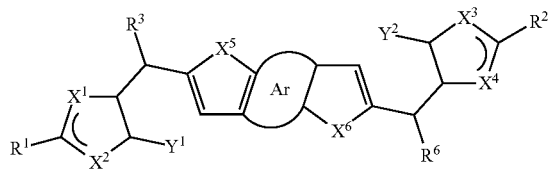

In the above Chemical Formula 1-1, $X^1$, $X^2$, $X^3$, $X^4$, $X^5$, $X^6$, $R^1$, $R^2$, $R^3$, and $R^6$ are the same as in the Chemical Formula 1, $Y^1$ is an acyl group (—C(=O)$R^4$, wherein $R^4$ is the same as in the Chemical Formula 1) or a halogen (e.g., —Br), and $Y^2$ is an acyl group (—C(=O)$R^5$, wherein $R^5$ is the same as in the Chemical Formula 1) or a halogen (e.g., —Br). For example, the fused polycyclic heteroaromatic compound may be synthesized according to the following Reaction Scheme 1, but is not specifically limited thereto.

mide, N-methylpyrrolidinone, and/or tetrahydrofuran. The catalyst for dehydration in the last step may be an acidic catalyst (e.g., Amberlyst® 15 (manufactured by Sigma-Aldrich)).

A person of ordinary skill in the art may adjust the molecular weight of the fused polycyclic heteroaromatic compound obtained from the synthesis according to example embodiments depending upon the usage and the case, for example, the molecular weight is about 350 to about 3000.

According to example embodiments, an organic thin film may include the fused polycyclic heteroaromatic compound and an electronic device may include the organic thin film.

The organic thin film according to example embodiments may include the fused polycyclic heteroaromatic compound, and so may be applied to an organic semiconductor layer for an electronic device, or a carrier transport layer (e.g., a channel layer). The electronic device including the same may have desirable electrical properties (e.g., higher charge mobility) as well as desirable processibility and workability.

[Reaction Scheme 1]

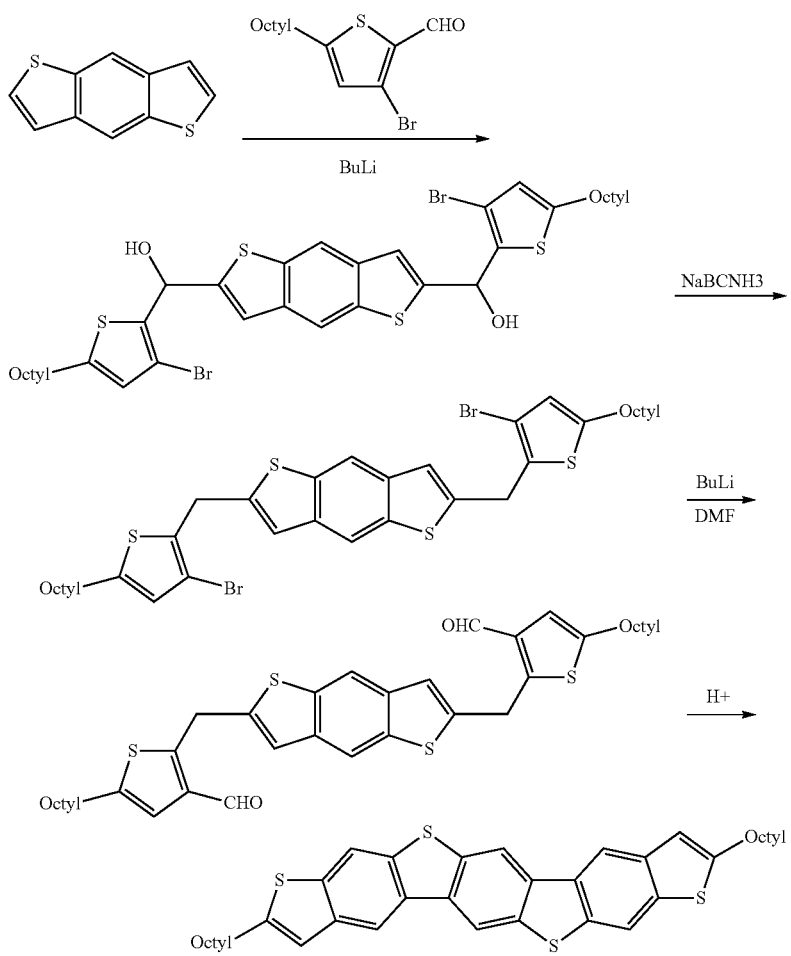

Reaction Scheme 1 may be performed using a heteroaromatic ring compound substituted with bromine at about −78° C. to room temperature (about 23° C. to about 25° C.) while being exposed to air or a nitrogen atmosphere. The solvent may include the commonly used toluene, dimethyl forma- The organic thin film may be manufactured by depositing the fused polycyclic heteroaromatic compound on a substrate according to the general method or dissolving the fused polycyclic heteroaromatic compound in an organic solvent and then coating the same at room temperature according to a solution process. If required, heating treatment may be performed after the deposition or coating process to further enhance the densification and uniformity of the thin film.

Particularly, the organic solvent may include at least one type of general organic solvent, for example, at least one type of an aliphatic hydrocarbon solvent (e.g., hexane or heptane); an aromatic hydrocarbon solvent (e.g., toluene, pyridine, quinoline, anisole, mesitylene or xylene); a ketone-based solvent (e.g., methyl isobutyl ketone, 1-methyl-2-pyrrolidinone, cyclohexanone, or acetone); an ether-based solvent (e.g., tetrahydrofuran or isopropyl ether); an acetate-based solvent (e.g., ethyl acetate, butyl acetate, or propylene glycol methyl ether acetate); an alcohol-based solvent (e.g., isopropyl alcohol or butanol); an amide-based solvent (e.g., dimethyl acetamide or dimethyl formamide); a silicone-based solvent; and a mixture of foregoing solvents. The amount of the fused polycyclic heteroaromatic compound dissolved in the organic solvent may be adequately selected and determined by a person of ordinary skill in the art, for example, in a range of about 0.01 wt % to about 50 wt % in the total solvent in view of the solubility and a coating property.

The method of providing an organic thin film may include thermal deposition, vacuum deposition, laser deposition, screen printing, printing, imprinting, spin casting, dipping, inkjetting, roll coating, flow coating, drop casting, spray coating, and/or roll printing, but is not limited thereto. The heat treatment may be performed at about 80 to about 250° C. for about 1 minute to about 2 hours, but is not limited thereto.

The thickness of the organic thin film may be adjusted according to the usage and the case considering the types of the used compound and solvent by a person of ordinary skill in the art, for example, in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, and/or a sensor, and the organic thin film may be applied to each device according to the general process commonly known in the art.

For example, the transistor includes a gate electrode disposed on a substrate; a source electrode and a drain electrode facing each other and defining a channel region; an insulation layer electrically insulating the source electrode and drain electrode and the gate electrode; and an active layer including the fused polycyclic heteroaromatic compound formed in the channel region.

The active layer may be obtained by depositing the fused polycyclic heteroaromatic compound, or applying a composition including the fused polycyclic heteroaromatic compound to a solution process (e.g., screen printing, printing, spin coating, dipping, or ink jetting). When the active layer is formed by the solution process, the process cost may be reduced, and a relatively wide area device may be effectively manufactured.

Figure 2:
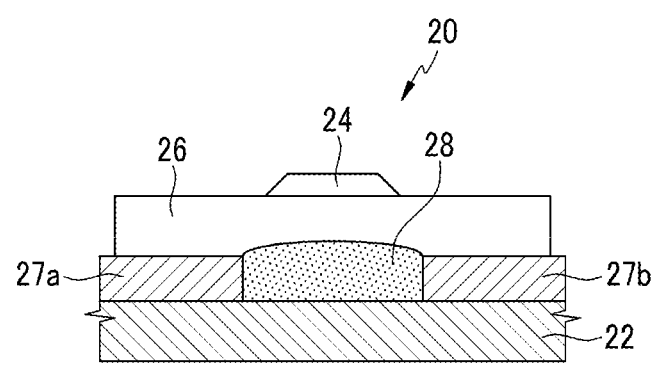
FIG. 2 is a schematic cross-sectional view of a transistor according to example embodiments.

FIGS. 1 and 2 are schematic cross-sectional views showing a transistor according to example embodiments. The transistor according to example embodiments may be a thin film transistor. The thin film transistor may be a thin film having a thickness of several nanometers to several microns.

Referring to FIG. 1, a transistor 10 may include a substrate 12, a gate electrode 14 disposed on the substrate, and an insulation layer 16 covering the gate electrode 14. On the insulation layer 16, a source electrode 17a and a drain electrode 17b defining a channel region may be provided, and an active layer 18 may be provided in the channel region. The active layer 18 may include the fused polycyclic heteroaromatic compound.

Referring to FIG. 2, a transistor 20 may include a source electrode 27a and a drain electrode 27b defining a channel region and that are formed on a substrate 22, and an active layer 28 formed on the channel region. The active layer 28 may include the fused polycyclic heteroaromatic compound. An insulation layer 26 may be formed to cover the source electrode 27a, the drain electrode 27b, and the active layer 28, and a gate electrode 24 may be formed thereon.

The substrates 12 and 22 may include an inorganic material, an organic material, or a composite of an inorganic material and an organic material. The organic material may include, for example, a plastic (e.g., polyethylene naphthalate (PEN), polyethylene terephthalate (PET), polycarbonate, polyvinyl alcohol, polyacrylate, polyimide, polynorbornene, and polyethersulfone (PES)), and the inorganic material may include, for example, glass or metal.

In addition, the gate electrodes 14 and 24, source electrodes 17a and 27a, and drain electrodes 17b and 27b may include a generally-used metal, for example, gold (Au), silver (Ag), aluminum (Al), nickel (Ni), or indium tin oxide (ITO), but are not limited thereto.

The insulation layers 16 and 26 may include a generally-used insulator having a high dielectric constant, for example, a ferroelectric insulator (e.g., $Ba_{0.33}Sr_{0.66}TiO_3$ (BST, barium strontium titanate), $Al_2O_3$, $Ta_2O_5$, $La_2O_5$, $Y_2O_3$, and/or $TiO_2$); an inorganic insulator (e.g., $PbZr_{0.33}Ti_{0.66}O_3$ (PZT) $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$ (x is determined depending on valence of Si), and/or AlON (aluminum oxynitride)); or an organic insulator (e.g., polyimide, benzocyclobutene (BCB), parylene, polyacrylate, polyvinyl alcohol, and/or polyvinylphenol), but are not limited thereto. Although it is not mentioned above, the inorganic insulator disclosed in U.S. Pat. No. 5,946,551 and the organic insulator disclosed in U.S. Pat. No. 6,232,157 may be used for the insulation layers 16 and 26.

Hereinafter, the embodiments are illustrated in more detail with reference to examples. However, the following are example embodiments and are not limiting.

Example 1

Preparation of Fused Polycyclic Heteroaromatic Compound

The fused polycyclic heteroaromatic compound is synthesized as shown in the following Reaction Scheme 2.

[Reaction Scheme 2]

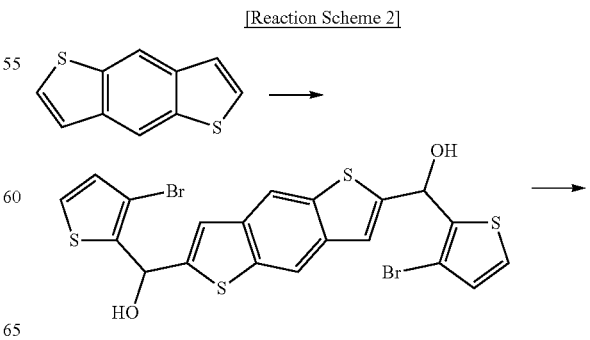

1

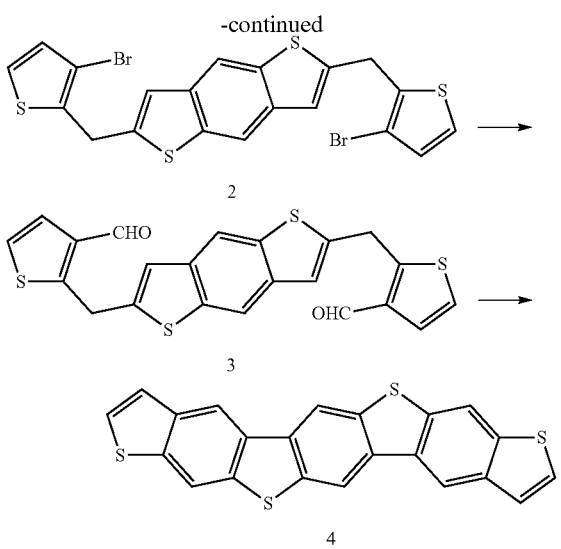

Synthesis of Compound 1:

Benzodithiophene (5.29 g, 28 mmol) is dissolved in 100 mL of dry THF (tetrahydrofuran), the resultant is added to 100 mL of an anhydrous diethyl ether solution including butyl lithium (25 mL of 2.5 M in hexane solution) cooled at 0° C. in a dropwise fashion, a temperature is increased slowly, and the resultant is agitated at room temperature for 2 hours. 3-bromo-thieno[3,2:b]thiophene-2-aldehyde (12 g, 62 mmol) is added to the turbid solution in a dropwise fashion and is agitated overnight. 100 ml of an ammonium chloride saturated aqueous solution is added thereto, precipitated materials are filtered, and the resultant is washed with water and diethyl ether to obtain a compound 1 (yield: 70%).

$^1$H NMR (300 MHz, CDCl$_3$): δ ppm 8.11 (d, 2H), 7.32 (d, 2H), 7.27 (d, 2H), 6.98 (d, 2H), 6.47 (d, 2H), 2.79 (d, 2H); $^{13}$CNMR (75.5 MHz, CDCl$_3$): 6 ppm 146.7, 140.7, 137.2, 137.1, 130.1, 126.0, 120.8, 117.2, 109.0, 68.6.

Synthesis of Compound 2:

The diol compound 1 (4.66 g, 8.15 mmole) is dissolved in 400 mL of dichloromethane and ZnI$_2$ (8.3 g, 26 mmole) and NaCNBH$_3$ (7.2 g, 114 mmole) are slowly added thereto. The resulting mixture is agitated at room temperature for 24 hours, and then passes through a Celite pad. The filtered resultant is washed with an ammonium chloride saturated solution and water, respectively, dried with MgSO$_4$, and concentrated under reduced pressure to obtain yellow oil. The yellow oil is purified with a silica chromatography to obtain a compound 2 (yield: 77%).

$^1$H NMR (300 MHz, CDCl$_3$): δ ppm 8.02 (s, 2H), 7.20 (d, 2H), 7.07 (d, 2H), 6.96 (d, 2H), 4.38 (s, 4H).

Synthesis of Compound 3:

THF solution (50 mL) including the compound 2 (1.4 g, 2.6 mmole) dissolved therein is added to a THF solution (50 mL) including t-butyl lithium (1.7M, 4.5 mL, 7.7 mmole) cooled to −78° C., in a dropwise fashion. The resultant is agitated at −78° C. for about 30 minutes, and DMF (1 mL) is added followed by agitating for about 1 hour. Water is poured thereto to complete a reaction, 100 mL of ethyl acetate is added, the resultant is washed with water and brine, and an organic layer is dried with MgSO$_4$, and concentrated under reduced pressure to obtain colorless oil. The colorless oil is purified with a silica chromatography to obtain a compound 3 (yield: 60%).

$^1$H NMR (300 MHz, CDCl$_3$): δ ppm 10.1 (s, 2H), 8.04 (s, 2H), 7.45 (d, 2H), 7.19 (d, 2H), 7.10 (s, 2H), 4.80 (s, 4H); $^{13}$C NMR (75.5 MHz, CDCl$_3$): 6 ppm 184.7, 152.7, 142.8, 137.3, 137.2, 136.9, 128.2, 124.2, 121.5, 116.4, 29.5.

Synthesis of Compound 4:

The compound 3 (0.35 g) is dissolved in 30 mL of benzene, Amberlyst® 15 (manufactured by Sigma-Aldrich) (0.5 g) is added thereto, the mixture is agitated while refluxing and water is removed using a Dean-Stark trap. After 24 hours, a yellow solid is precipitated. After a temperature is decreased into room temperature, Amberlyst® 15 is precipitated, suspended materials are removed using a filter to obtain a compound 4 as a yellow solid (yield: 60%).

Figure 3:
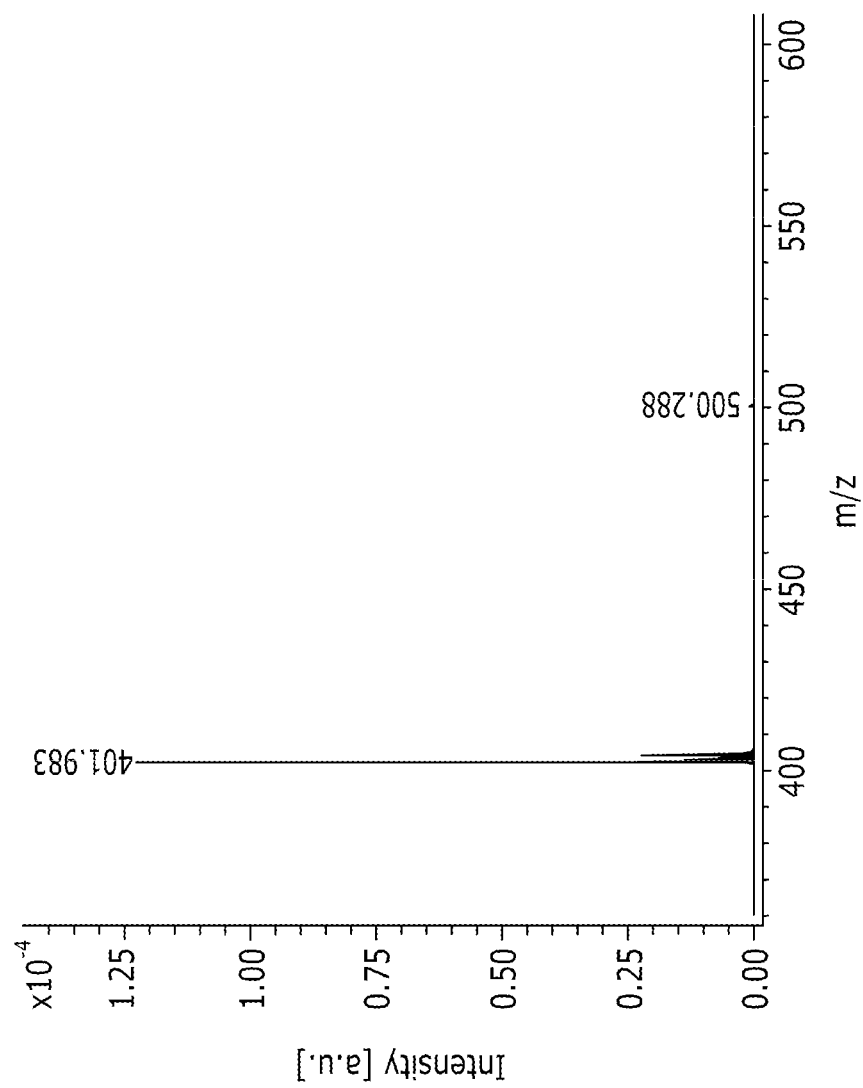
FIG. 3 shows a Maldi-MS spectrum of the compound 4 according to Example 1.

Maldi-MS spectrum (Ultraflex III TOF/TOF 200 mass spectrometer, Bruker Corporation) of the compound 4 is shown in FIG. 3.

Example 2

Manufacture of Organic Thin Film Transistor Using Fused Polycyclic Heteroaromatic Compound A silicon substrate covered with a 3000 Å silicon oxide film is rinsed with isopropyl alcohol for 10 minutes The rinsed silicon substrate is treated with oxygen plasma, dipped in a octadecyl trichlorosilane solution that is diluted to a 5 mM concentration in hexane, for 30 minutes, is rinsed with hexane and ethanol, baked at 120° C. for 30 minutes, and washed with an ultrasonic wave in a chloroform solution. The washed silicon substrate is dried and the fused polycyclic heteroaromatic compound 4 according to Example 1 is applied at a thickness of 700 Å using a vacuum thermal deposition. Gold (Au) as a source-drain electrode is sputtered at a thickness of 1000 Å thereon to fabricate an OTFT device.

Figure 4:
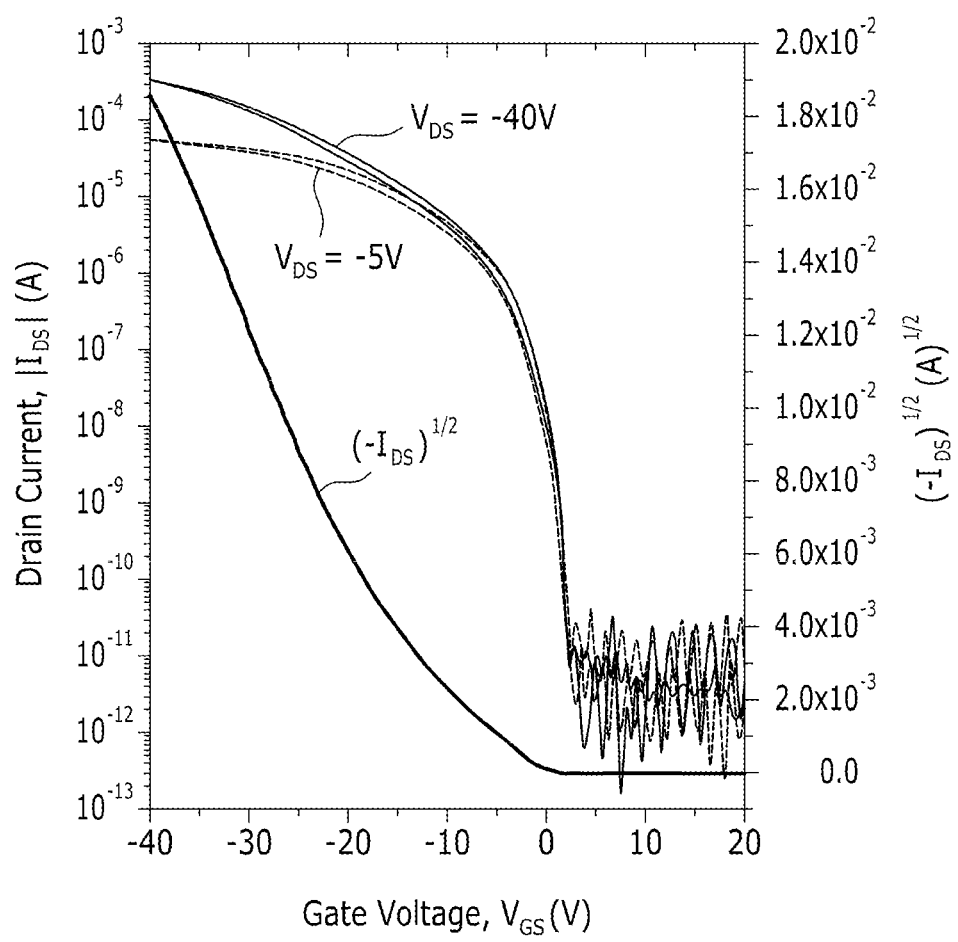
FIG. 4 shows current transfer characteristics of the organic thin film transistor according to Example 2.

Current transfer characteristics of the OTFT device according to Example 2 is measured using a semiconductor characterization system (KEITHLEY, 4200-SCS) and the results are shown in FIG. 4. As shown in FIG. 4, the OTFT device according to Example 2 has improved current transfer characteristics.

While this disclosure has been described in connection with what is presently considered to be practical example embodiments, it is to be understood that the inventive concepts are not limited to the disclosed embodiments, but, on the contrary, are intended to cover various modifications and equivalent arrangements included within the spirit and scope of the appended claims.

What is claimed is:

1. A fused polycyclic heteroaromatic compound comprising a structural unit represented by the following Chemical Formula 1:

[Chemical Formula 1]

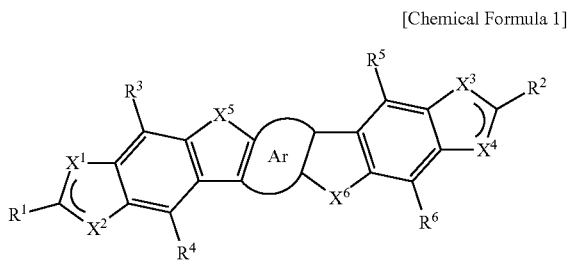

wherein, in the above Chemical Formula 1,

Ar is one of a substituted or unsubstituted benzene, a substituted or unsubstituted naphthalene, and a substituted or unsubstituted anthracene, each of $X^1$ to $X^4$ are independently one of O, S, Se, Te, N—$R^a$, and $CR^b$, wherein each of $R^a$ and $R^b$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —C(=O)$R^{13}$, wherein $R^{13}$ is a substituted or unsubstituted $C_1$ to $C_{30}$ alkyl group, —S(=O)$_2R^{14}$, wherein $R^{14}$ is a substituted or unsubstituted $C_1$ to $C_{30}$ alkyl group, and —NHC(=O)$OR^{15}$, wherein $R^{15}$ is a substituted or unsubstituted $C_1$ to $C_{30}$ alkyl group, at least one of $X^1$ and $X^2$ is selected from O, S, Se, and Te,
at least one of $X^3$ and $X^4$ is selected from O, S, Se, and Te,
each of $X^5$ and $X^6$ are independently one of O, S, Se, Te, and $CR^bR^c$ wherein each of $R^b$ to $R^c$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —C(=O)$R^{13}$, wherein $R^{13}$ is a substituted or unsubstituted $C_1$ to $C_{30}$ alkyl group, —S(=O)$_2R^{14}$, wherein $R^{14}$ is a substituted or unsubstituted $C_1$ to $C_{30}$ alkyl group, and —NHC(=O)$OR^{15}$, wherein $R^{15}$ is a substituted or unsubstituted $C_1$ to $C_{30}$ alkyl group, and each of $R^1$ to $R^6$ are independently one of hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

2. The fused polycyclic heteroaromatic compound of claim 1, wherein the fused polycyclic heteroaromatic compound is represented by the following Chemical Formula 1A:

[Chemical Formula 1A]

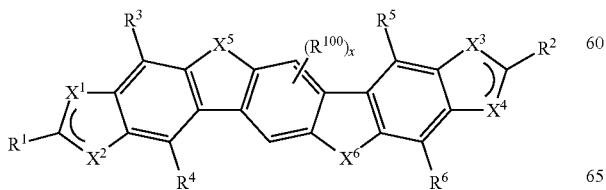

wherein, in the above Chemical Formula 1A,
each of $X^1$ to $X^4$ are independently one of O, S, Se, Te, N—$R^a$, and $CR^b$, wherein each of $R^a$ and $R^b$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group), a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —C(=O)$R^{13}$, wherein $R^{13}$ is a substituted or unsubstituted $C_1$ to $C_{30}$ alkyl group, —S(=O)$_2R^{14}$, wherein $R^{14}$ is a substituted or unsubstituted $C_1$ to $C_{30}$ alkyl group, and —NHC(=O)$OR^{15}$, wherein $R^{15}$ is a substituted or unsubstituted $C_1$ to $C_{30}$ alkyl group, at least one of $X^1$ and $X^2$ is selected from O, S, Se, and Te,
at least one of $X^3$ and $X^4$ is selected from O, S, Se, and Te,
each of $X^5$ and $X^6$ are independently one of O, S, Se, Te, and $CR^bR^c$ wherein each of $R^b$ to $R^c$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —C(=O)$R^{13}$, wherein $R^{13}$ is a substituted or unsubstituted $C_1$ to $C_{30}$ alkyl group, —S(=O)$_2R^{14}$, wherein $R^{14}$ is a substituted or unsubstituted $C_1$ to $C_{30}$ alkyl group, and —NHC(=O)$OR^{15}$, wherein $R^{15}$ is a substituted or unsubstituted $C_1$ to $C_{30}$ alkyl group, each of $R^1$ to $R^6$ are independently one of hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, $R^{100}$ is hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, or a substituted or unsubstituted $C_2$ to $C_{30}$ heteroaryl group, and x is an integer of 1 or 2.

3. The fused polycyclic heteroaromatic compound of claim 2, wherein, in Chemical Formula 1A, each of $R^1$ to $R^6$ are independently one of a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

4. The fused polycyclic heteroaromatic compound of claim 2, wherein, in Chemical Formula 1A, one of $X^1$ and $X^2$ and one of $X^3$ and $X^4$ are sulfur (S).

5. The fused polycyclic heteroaromatic compound of claim 1, wherein the fused polycyclic heteroaromatic compound is represented by one of the following Chemical Formulae 1B to 1D:

[Chemical Formula 1B]

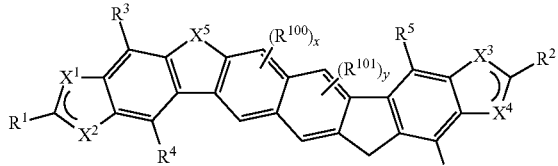

[Chemical Formula 1C]

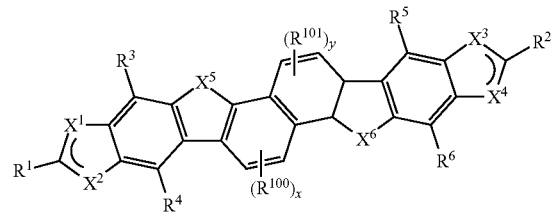

[Chemical Formula 1D]

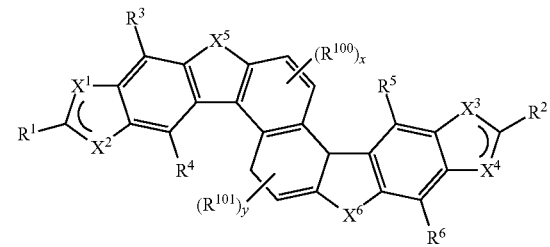

wherein, in the above Chemical Formulae 1B to 1D, each of $X^1$ to $X^4$ are independently one of O, S, Se, Te, N—$R^a$, and $CR^b$, wherein each of $R^a$ and $R^b$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —$C(=O)R^{13}$, wherein $R^{13}$ is a substituted or unsubstituted $C_1$ to $C_{30}$ alkyl group, —$S(=O)_2R^{14}$, wherein $R^{14}$ is a substituted or unsubstituted $C_1$ to $C_{30}$ alkyl group, and —$NHC(=O)OR^{15}$, wherein $R^{15}$ is a substituted or unsubstituted $C_1$ to $C_{30}$ alkyl group, at least one of $X^1$ and $X^2$ is selected from O, S, Se, and Te,
at least one of $X^3$ and $X^4$ is selected from O, S, Se, and Te,
each of $X^5$ and $X^6$ are independently one of O, S, Se, Te, and $CR^bR^c$ wherein each of $R^b$ to $R^c$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —$C(=O)R^{13}$, wherein $R^{13}$ is a substituted or unsubstituted $C_1$ to $C_{30}$ alkyl group, —$S(=O)_2R^{14}$, wherein $R^{14}$ is a substituted or unsubstituted $C_1$ to $C_{30}$ alkyl group, and —$NHC(=O)OR^{15}$, wherein $R^{15}$ is a substituted or unsubstituted $C_1$ to $C_{30}$ alkyl group, each of $R^1$ to $R^6$ are independently one of hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, each of $R^{100}$ and $R^{101}$ are independently one of hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_6$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, and x and y are integers of 1 or 2.

6. The fused polycyclic heteroaromatic compound of claim 5, wherein, in Chemical Formulae 1B to 1D, each of $R^1$ to $R^6$ are independently one of a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

7. The fused polycyclic heteroaromatic compound of claim 5, wherein, in Chemical Formulae 1B to 1D, one of $X^1$ and $X^2$ and one of $X^3$ and $X^4$ are sulfur (S).

8. The fused polycyclic heteroaromatic compound of claim 1, wherein the fused polycyclic heteroaromatic compound is represented by one of the following Chemical Formulae 1E to 1G:

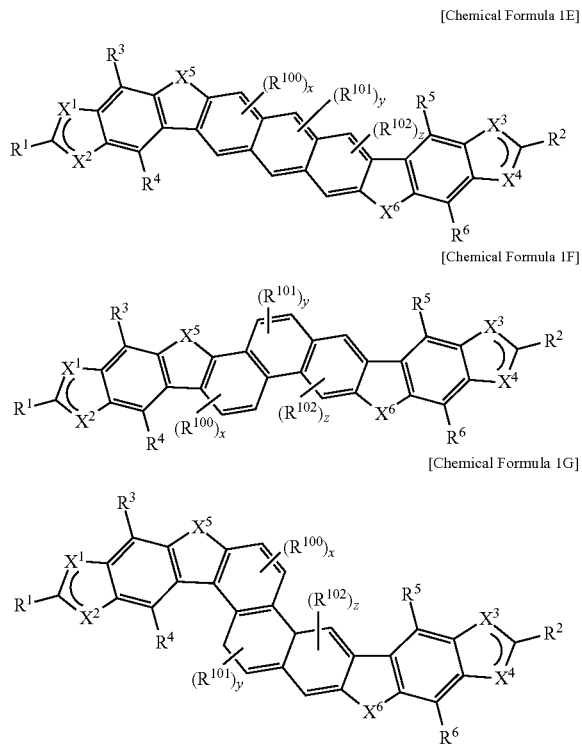

[Chemical Formula 1E]

[Chemical Formula 1F]

[Chemical Formula 1G]

wherein, in the above Chemical Formulae 1E to 1G, each of $X^1$ to $X^4$ are independently one of O, S, Se, Te, N—$R^a$, and $CR^b$, wherein each of $R^a$ and $R^b$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_6$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —C(=O)$R^{13}$, wherein $R^{13}$ is a substituted or unsubstituted $C_1$ to $C_{30}$ alkyl group, —S(=O)$_2R^{14}$, wherein $R^{14}$ is a substituted or unsubstituted $C_1$ to $C_{30}$ alkyl group, and —NHC(=O)O$R^{15}$, wherein $R^{15}$ is a substituted or unsubstituted $C_1$ to $C_{30}$ alkyl group, at least one of $X^1$ and $X^2$ is selected from O, S, Se, and Te, at least one of $X^3$ and $X^4$ is selected from O, S, Se, and Te, each of $X^5$ and $X^6$ are independently one of O, S, Se, Te, and $CR^bR^c$ wherein each of $R^b$ to $R^c$ are independently one of hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, —$OR^{11}$, wherein $R^{11}$ is a substituted or unsubstituted $C_5$ to $C_{30}$ aryl group, a substituted or unsubstituted $C_4$ to $C_{30}$ cycloalkyl group, —$OR^{12}$, wherein $R^{12}$ is a substituted or unsubstituted $C_4$ to $C_{30}$ cycloalkyl group, a substituted or unsubstituted $C_2$ to $C_{30}$ heteroaryl group, —C(=O)$R^{13}$, wherein $R^{13}$ is a substituted or unsubstituted $C_1$ to $C_{30}$ alkyl group, —S(=O)$_2R^{14}$, wherein $R^{14}$ is a substituted or unsubstituted $C_1$ to $C_{30}$ alkyl group, and —NHC(=O)O$R^{15}$, wherein $R^{15}$ is a substituted or unsubstituted $C_1$ to $C_{30}$ alkyl group, and each of $R^1$ to $R^6$ are independently one of hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, each of $R^{100}$ to $R^{102}$ are independently one of hydrogen, —F, —Cl, —Br, —I, a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group, and x, y, and z are integers of 1 or 2.

9. The fused polycyclic heteroaromatic compound of claim 8, wherein, in Chemical Formulae 1E to 1G, each of $R^1$ to $R^6$ are independently one of a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

10. The fused polycyclic heteroaromatic compound of claim 8, wherein, in Chemical Formulae 1E to 1G, one of $X^1$ and $X^2$ and one of $X^3$ and $X^4$ are sulfur (S).

11. The fused polycyclic heteroaromatic compound of claim 1, wherein, in Chemical Formula 1, an atom of each of $X^1$ and $X^4$, and $X^2$ and $X^3$ is positioned symmetrically to each other.

12. The fused polycyclic heteroaromatic compound of claim 1, wherein, in Chemical Formula 1, one of $X^1$ and $X^2$ and one of $X^3$ and $X^4$ are sulfur (S).

13. The fused polycyclic heteroaromatic compound of claim 1, wherein the fused polycyclic heteroaromatic compound has an average molecular weight of about 350 to about 3000.

14. The fused polycyclic heteroaromatic compound of claim 1, wherein, in Chemical Formula 1, each of $R^1$ to $R^6$ are independently one of a substituted or unsubstituted linear or branched $C_1$ to $C_{30}$ alkyl group, a substituted or unsubstituted linear or branched $C_2$ to $C_{30}$ alkenyl group, a substituted or unsubstituted linear or branched $C_2$ to $C_{30}$ alkynyl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, a substituted or unsubstituted $C_2$ to $C_{30}$ heterocycloalkyl group, a substituted or unsubstituted $C_6$ to $C_{30}$ aryl group, and a substituted or unsubstituted $C_2$ to $C_{30}$ heteroaryl group.

15. An organic thin film comprising the fused polycyclic heteroaromatic compound according to claim 1.

16. An electronic device comprising the fused polycyclic heteroaromatic compound according to claim 1.

17. The electronic device of claim 16, wherein the electronic device is one of a transistor, an organic light emitting diode (OLED), a photovoltaic device, a solar cell, a laser device, a memory, and a sensor.

18. The electronic device of claim 16, further comprising:
a transistor including an active layer formed of the fused polycyclic heteroaromatic compound in a channel region.

\* \* \* \* \*